United States Patent
Tarajano et al.

(10) Patent No.: US 11,633,307 B2
(45) Date of Patent: Apr. 25, 2023

(54) POROUS FORMULATION STORAGE CUSHION, FORMULATION DELIVERY SYSTEM, AND METHOD OF MANUFACTURING A POROUS FORMULATION STORAGE CUSHION

(71) Applicant: L'Oreal, Paris (FR)

(72) Inventors: Lemis Tarajano, Brooklyn, NY (US); Karin Kaskiel, New York, NY (US); Zachary Mahoney, Freehold, NJ (US); Kyoo Jin Park, Leonia, NJ (US); Youn Jong Lee, Kawasaki (JP)

(73) Assignee: L'Oreal, Paris (FR)

( * ) Notice: Subject to any disclaimer, the term of this patent is extended or adjusted under 35 U.S.C. 154(b) by 1123 days.

(21) Appl. No.: 16/260,872

(22) Filed: Jan. 29, 2019

(65) Prior Publication Data
US 2020/0237568 A1 Jul. 30, 2020

(51) Int. Cl.
*A61F 13/15* (2006.01)
*A61L 15/42* (2006.01)

(52) U.S. Cl.
CPC ...... *A61F 13/15203* (2013.01); *A61L 15/425* (2013.01); *A61F 2013/15463* (2013.01); *A61F 2013/15495* (2013.01); *A61F 2013/15528* (2013.01)

(58) Field of Classification Search
CPC ...... A61F 13/15203; A61F 2013/15463; A61F 2013/15495; A61F 2013/15528; A61L 15/425
See application file for complete search history.

(56) References Cited

U.S. PATENT DOCUMENTS

| 5,121,329 | A | 6/1992 | Crump |
| 6,030,138 | A * | 2/2000 | Losier .................. B65D 47/42 401/265 |
| 7,077,638 | B2 | 7/2006 | Leyden et al. |
| 8,141,717 | B2 | 3/2012 | Wingo et al. |
| 8,147,910 | B2 | 4/2012 | Kritchman |

(Continued)

FOREIGN PATENT DOCUMENTS

| EP | 833237 A2 | 4/1998 |
| EP | 1015215 A1 | 7/2000 |

(Continued)

OTHER PUBLICATIONS

International Search Report and Written Opinion dated Mar. 19, 2020, issued in corresponding International Application No. PCT/US2019/066081, filed Dec. 12, 2019, 22 pages.

(Continued)

*Primary Examiner* — Jessica Arble
(74) *Attorney, Agent, or Firm* — Christensen O'Connor Johnson Kindness PLLC (57) ABSTRACT

Porous formulation storage cushion, formulation delivery systems including porous formulation storage cushions, and methods of additively manufacturing a porous formulation storage cushions are described. In an embodiment, the porous formulation storage cushion defines a plurality of pores configured to absorb a formulation, such as through wicking the formulation through capillary action. In an embodiment, the plurality of pores is configured to define a capillary force gradient along a length of the porous formulation storage cushion.

29 Claims, 10 Drawing Sheets (56) References Cited

U.S. PATENT DOCUMENTS

| | | |
|---|---|---|
| 8,245,757 B2 | 8/2012 | Crump et al. |
| 9,233,506 B2 | 1/2016 | Leavitt |
| 9,724,866 B2 | 8/2017 | Hopkins et al. |
| 9,944,016 B2 | 4/2018 | Lewicki |
| 10,052,813 B2 | 8/2018 | Armijo et al. |
| 10,195,635 B2 | 2/2019 | Sporrer |
| 10,881,591 B2 | 1/2021 | Harris et al. |
| 11,141,951 B2 | 10/2021 | Mao et al. |
| 2008/0057103 A1* | 3/2008 | Roorda .................. A61L 31/10 424/425 |
| 2009/0180826 A1* | 7/2009 | Guay .................... A45D 34/04 401/207 |
| 2018/0250748 A1 | 9/2018 | Page |

FOREIGN PATENT DOCUMENTS

| | | | |
|---|---|---|---|
| EP | 1099534 A2 | 5/2001 | |
| EP | 3019648 A1 | 5/2016 | |
| EP | 3063340 A1 | 9/2016 | |
| WO | 2004/062423 A1 | 7/2004 | |
| WO | 2006/069744 A1 | 7/2006 | |
| WO | 201817330 A1 | 1/2018 | |
| WO | 2018/231537 A1 | 12/2018 | |
| WO | WO-2018231537 A1 * | 12/2018 | ............. A45D 37/00 |

OTHER PUBLICATIONS

Office Action dated Feb. 13, 2023, in Japanese Application No. 2021-543422, filed Dec. 12, 2019, 4 pages.

\* cited by examiner

POROUS FORMULATION STORAGE CUSHION, FORMULATION DELIVERY SYSTEM, AND METHOD OF MANUFACTURING A POROUS FORMULATION STORAGE CUSHION

SUMMARY

In an aspect, the present disclosure provides a formulation delivery system, generally including a body portion configured to carry a formulation; a porous applicator configured to absorb the formulation; and a porous formulation storage cushion defining a plurality of pores configured to absorb the formulation, wherein the porous formulation storage cushion is carried by the body portion, wherein the plurality of pores is configured to define a capillary force gradient along a length of the porous formulation storage cushion.

In another aspect, the present disclosure provides method of additively manufacturing a porous formulation storage cushion defining a plurality of pores configured to absorb a formulation, the method generally including depositing a first layer of a material with an additive manufacturing assembly; and depositing a second layer of the material with the additive manufacturing assembly to define a plurality of pores, wherein the plurality of pores is configured to define a capillary force gradient along a length of the porous formulation storage cushion.

In another aspect, the present disclosure provides a method of transporting a formulation, the method generally including transporting the formulation from a base portion of a porous formulation storage cushion through a plurality of pores to an application surface of the porous formulation storage cushion by capillary action; and transporting the formulation from the application surface through pores of a porous applicator, wherein the plurality of pores is configured to define a capillary force gradient along a length of the porous formulation storage cushion.

In accordance with any of the embodiments disclosed herein, the porous formulation storage cushion comprises an additively manufactured porous structure. In accordance with any of the embodiments disclosed herein, the porous formulation storage cushion comprises a porous sintered material.

In accordance with any of the embodiments disclosed herein, the porous formulation storage cushion comprises a plurality of filaments, and wherein interstices between individual filaments of the plurality of filaments define the plurality of pores. In accordance with any of the embodiments disclosed herein, a thickness of filaments of the plurality of filaments varies along a length of the porous formulation storage cushion. In accordance with any of the embodiments disclosed herein, the plurality of pores defined by the plurality of filaments is configured to provide a directional wicking of the formulation through the plurality of pores.

In accordance with any of the embodiments disclosed herein, the plurality of pores is configured to provide a fluidic communication between the porous applicator and the formulation when the porous applicator is in contact with an application surface of the porous formulation storage cushion.

In accordance with any of the embodiments disclosed herein, a size of individual pores of the plurality of pores defines a pore-size gradient along a length of the porous formulation storage cushion. In accordance with any of the embodiments disclosed herein, a density of pores of the plurality of pores defines a pore-density gradient along a length of the porous formulation storage cushion.

In accordance with any of the embodiments disclosed herein, an application surface of the porous storage formulation cushion defines a first portion having a plurality of pores configured to place the porous applicator in fluidic contact with the formulation and a second portion free of pores.

In accordance with any of the embodiments disclosed herein, the formulation delivery system includes a formulation carried by the body portion and in a fluidic communication with the plurality of pores.

In accordance with any of the embodiments disclosed herein, the plurality of pores is configured to wick the formulation through a capillary action.

In accordance with any of the embodiments disclosed herein, the porous formulation storage cushion is configured to load a first portion of the porous applicator with a first amount of formulation and to load a second portion of the porous applicator with a second amount of formulation different than the first amount.

In accordance with any of the embodiments disclosed herein, the porous formulation storage cushion varies in stiffness across a length of the porous formulation storage cushion.

In accordance with any of the embodiments disclosed herein, an application surface of the porous formulation storage cushion comprises a porous lattice configured to contact the porous applicator. In accordance with any of the embodiments disclosed herein, the lattice has a stiffness different than a stiffness of other portions of the porous formulation delivery storage cushion.

This foregoing summary is provided to introduce a selection of concepts in a simplified form that are further described below in the Detailed Description. This summary is not intended to identify key features of the claimed subject matter, nor is it intended to be used as an aid in determining the scope of the claimed subject matter.

Aspects and many of the attendant advantages of the claimed subject matter will become more readily appreciated as the same become better understood by reference to the following detailed description, when taken in conjunction with the accompanying drawings.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

DETAILED DESCRIPTION

The following provides examples of porous formulation storage cushions, formulation delivery systems including porous formulation storage cushions, and methods of additively manufacturing porous formulation storage cushions.

A cosmetic container, such as a compact, may include a porous pad or cushion in which a formulation may be absorbed, such as for storage when not in use and for delivery to a porous applicator. Conventional porous pads or cushions include foams, compressed, fibers, or the like. Such conventional porous pads or cushions typically define pores having relatively even distributions of pore sizes and relatively even distributions of pore densities. Such even distributions of pore sizes and pore densities may be unsuitable to provide consistent loading of formulation onto a formulation applicator as the cosmetic container is used repeatedly and the formulation is depleted from within the formulation container. Likewise, such conventional porous pads or cushions may be unsuitable to selectively load portions of a formulation applicator for particular formulation application uses, such as where targeted application or an application gradient or pattern of formulation may be desirable.

Toward that end, the present disclosure provides a porous formulation storage cushion defining a plurality of pores configured to absorb a formulation, such as a liquid formulation, wherein the plurality of pores is configured to define a capillary force gradient along a length of the porous formulation storage cushion. As discussed further herein, such a porous formulation storage cushion may include an additively manufactured porous structure or a porous sintered material. Through the processes of additively manufacturing or sintering, a porous formulation storage cushion can be formed which includes variety of material properties such as pore-size gradients, pore-density gradients, stiffness gradients, and the like suitable to selectively tailor capillary force within the porous formulation storage cushion and formulation loading of an applicator in contact with the porous formulation storage cushion.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. Further, it will be appreciated that embodiments of the present disclosure may employ any combination of features described herein.

Figures 1A, 1B, 1C:
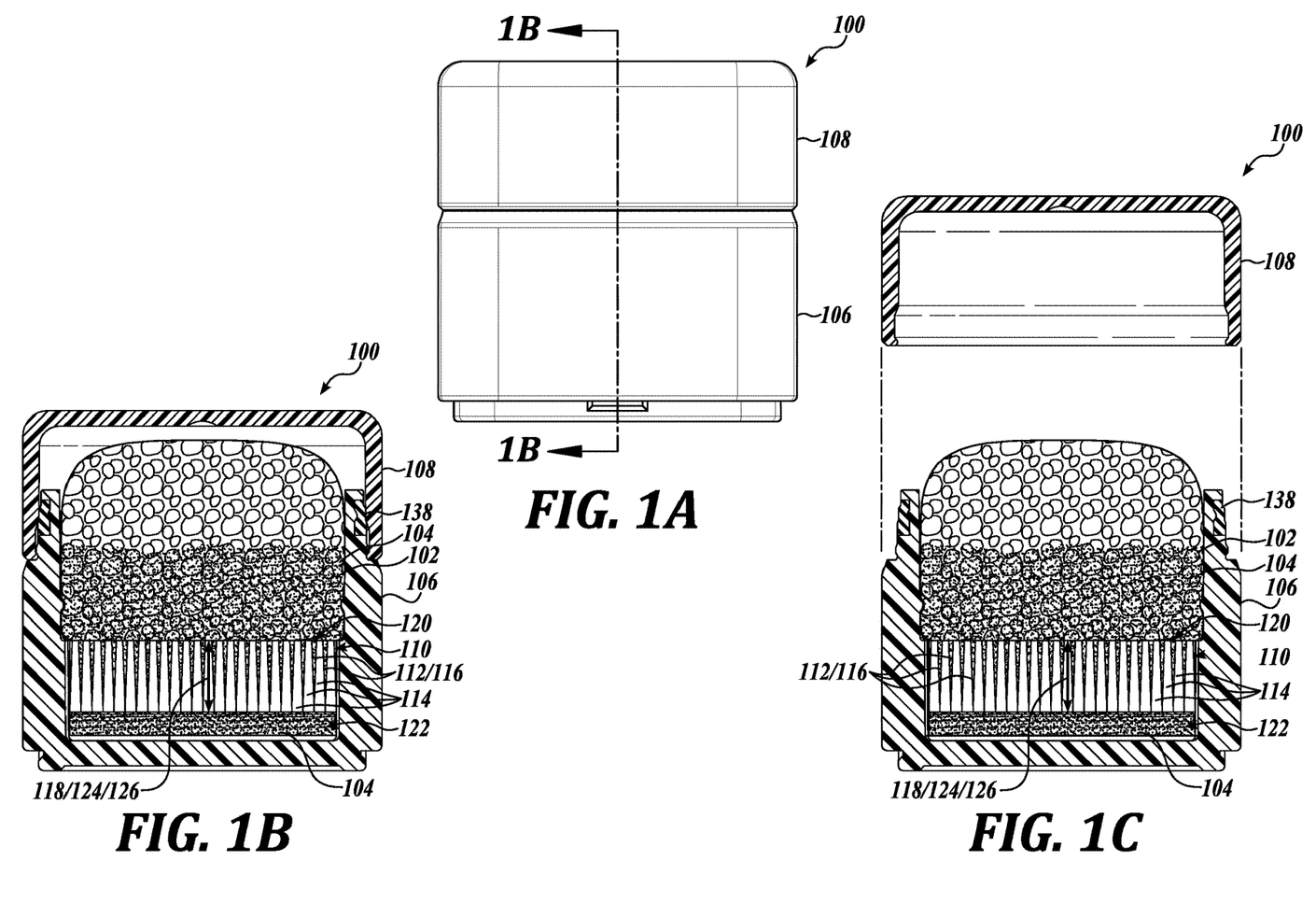
FIG. 1A is a side view of a formulation delivery system, in accordance with an embodiment of the disclosure.
FIG. 1B is a cross-section view of the formulation delivery system of FIG. 1A, shown in a closed position.
FIG. 1C is another cross-section view of the formulation delivery system of FIG. 1A, shown in an open position.

Turning now to FIGS. 1A and 1B, a formulation delivery system 100, in accordance with an embodiment of the disclosure, is illustrated. FIG. 1A is a side view of a formulation delivery system 100. FIG. 1B is a cross-section view of the formulation delivery system 100 shown in a closed position. FIG. 1C is another cross-section view of the formulation delivery system 100 shown in an open position. As shown, the formulation delivery system 100 includes a porous applicator 102 disposed in a cap 108, a porous formulation storage cushion 110 disposed in a body portion 106, and a formulation 104. The porous formulation storage cushion 110 is shown to define a plurality of pores 112. In the illustrated embodiment, the plurality of pores 112 is configured to provide fluidic communication between the porous applicator 102 and the formulation 104 when the porous applicator 102 is in contact with an application surface 120 of the porous formulation storage cushion 110, such as when the cap 108 and body portion 106 are in a closed configuration. See, for example, FIG. 1C. In that regard, as the porous applicator 102 is placed in contact with an applicator surface of the porous formulation storage cushion 110, the porous applicator 102 is loaded with the formulation 104, such as through capillary action. As shown in FIG. 1C, the formulation delivery system 100 may be placed in an open position, such as to apply the formulation 104 with the porous applicator 102.

The formulation delivery system 100 is shown as a compact 100. It will be understood, however, that the formulation delivery systems of the present inventive technology can take other form factors for formulation delivery.

In an embodiment, the porous formulation storage cushion 110 comprises an additively manufactured porous structure (e.g., porous structures manufactured by 3D additive technologies). As discussed further herein with respect to the methods of the present inventive technology, additive manufacturing technology may be used to additively manufacture a porous formulation storage cushion 110. In this regard, a first layer of a material may be deposited, such as with a print head of an additive manufacturing assembly and, subsequently, a second layer of the material may be deposited on a surface of the first layer. Such additive steps of layered deposition may be repeated numerous times to assemble the porous formulation storage cushion 110. As also discussed further herein with respect to the methods of the present inventive technology, such additive layers may be shaped to define a plurality of pores 112 of the porous formulation storage cushion 110.

In the illustrated embodiment, the porous formulation storage cushion 110 includes a plurality of filaments 114, the interstices 116 of which define the plurality of pores 112. As discussed further herein, such plurality of filaments 114 may be suitable to be made through additive manufacturing. As shown, the formulation 104 is disposed in the plurality of pores 112 and in pores of the porous applicator 102, as well as about the base portion 122 of the porous formulation storage cushion 110. The formulation 104 may be drawn through capillary from a base portion 122 into the plurality of pores 112 of the porous formulation storage cushion 110 to the application surface 120 and into the pores of the porous applicator 102. As discussed further herein, the plurality of pores 112 may be configured to define a capillary force gradient along a length 118 of the porous formulation storage cushion 110, such as by defining a pore-size gradient 124 and/or a pore-density gradient 126.

While pores are illustrated as being defined by interstices 116 between filaments of a plurality of filaments 114, it will be understood that other pore configurations are possible. In that regard, pores of the porous formulation storage cushion 110 may be defined, for example, by apertures within the porous formulation storage cushion suitable to allow passage of a formulation 104 therethrough. Such can pores include, for example, channels, fluid passageways, capillaries, and the like, in addition to the interstices 116 between the plurality of filaments 114.

In an embodiment, structures of the additively manufactured porous formulation storage cushion 110 include lines or plates of declination defining a joint or interfacial layer between additively manufactured layers. Such lines or plates of declination may derive from the layer-on-layer manufacturing of the additive manufacturing assembly. In that regard, the lines or plates of declination may be disposed at an interface the sequentially deposited layers.

Figure 5A:
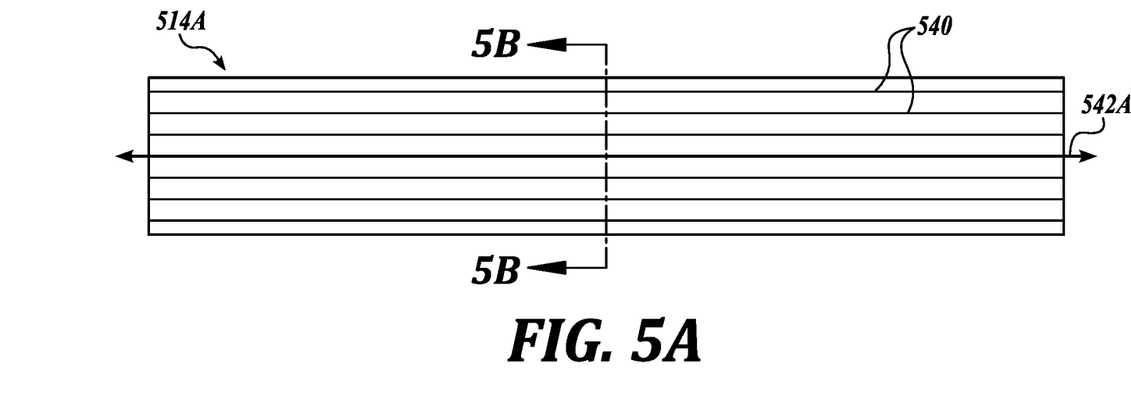
FIG. 5A is a side view of a filament, in accordance with an embodiment of the disclosure.
Figure 5B:
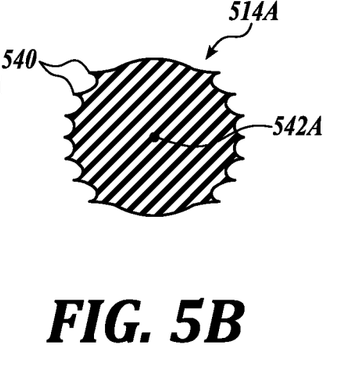
FIG. 5B is a top-down plan view of the filament of FIG. 5A.
Figure 5C:
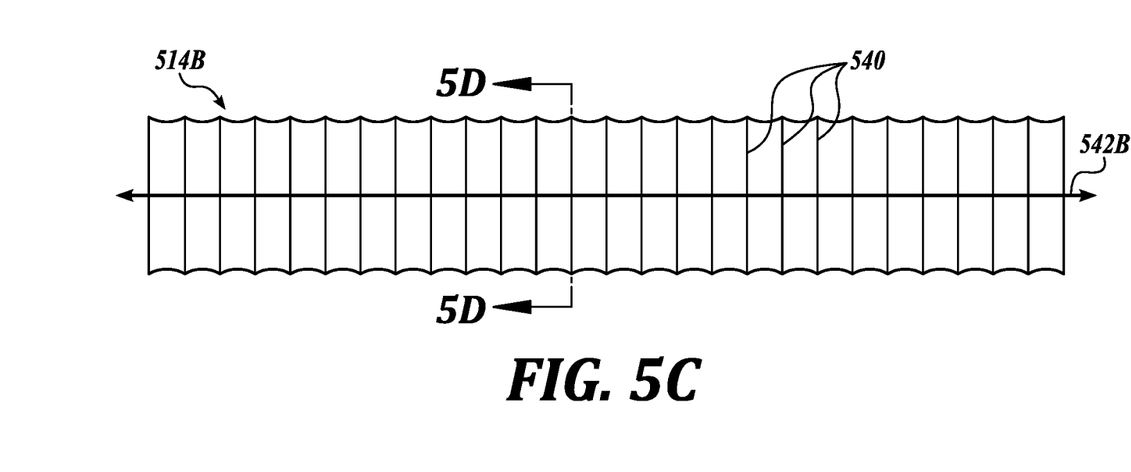
FIG. 5C is a side view of another filament, in accordance with an embodiment of the disclosure.
Figure 5D:
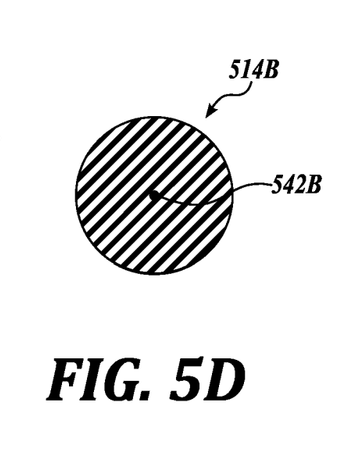
FIG. 5D is a top-down plan view of the filament of FIG. 5C.

Additively manufactured filaments 514A and 514B defining lines of declination 540, in accordance with an embodiment of the disclosure, are illustrated in FIGS. 5A-5D. In an embodiment, layers of material are deposited perpendicular to a major axis of the filament, as shown in FIGS. 5C and 5D, where lines of declination 540B are disposed perpendicular to a major axis 542B of filament 514B. Such plates of declination 540B perpendicular to major axis 542B of filament 514B may be suitable to slow wicking of a formulation along the major axis 542B. In this regard, wicking speeds may be tailored based upon an orientation of deposition relative to a major axis of a filament.

In an embodiment, layers of material are deposited parallel to a major axis of the filament, as shown in FIGS. 5A and 5B, where lines of declination 540A are disposed parallel to the major axis 542A of filament 514A. Such parallel lines of declination 540A may be suitable to aid in wicking of a formulation along the major axis 542A of the filament 514A, thus speeding the formulation through a porous formulation storage cushion containing filament 514A.

In an embodiment, the additively manufactured porous structure comprises a material selected from the group consisting of urethane methacrylate, cyanate ester, a silicone-urethane polymer mixture, rigid polyurethane, an epoxy, elastomeric polyurethane, flexible polyurethane, and combinations thereof.

In an embodiment, the porous formulation storage cushion comprises a porous sintered material. In an embodiment, such porous sintered materials define pores having a porosity gradient, such as a pore-density gradient and/or a pore-size gradient, as discussed further herein. Accordingly, in an embodiment, the porous sintered material defines a stiffness gradient. In an embodiment, the porous sintered material includes a polymeric porous sintered material. In an embodiment, the polymeric material is selected from the group consisting of polyethylene, polypropylene, polyethylene terephthalate. and combinations thereof.

Referring back to FIGS. 1A-1C, the formulation delivery system 100 is shown to include a formulation 104. In the illustrated embodiment, formulation delivery system 100 includes a formulation 104 carried by the body portion 106 and in contact with the porous formulation storage cushion 110. In an embodiment, the formulation 104 is a liquid formulation 104 configured to be in fluidic communication with one or more of the plurality of pores 112. In this regard, the plurality of pores 112 is configured to wick the formulation 104 through capillary action, such as to deliver the formulation 104 to an application surface 120 of the porous formulation storage cushion 110 for receipt by the porous applicator 102. In an embodiment, the formulation 104 is a liquid formulation 104 selected from the group consisting of foundation, moisturizer, sunscreen, concealer, contouring, and the like.

In an embodiment, the formulation delivery system 100 is configured to contain the formulation 104 within an interior portion of the formulation delivery system 100. In this regard, the formulation delivery system 100 may be suitable to be placed in a bag, a pocket, and the like without spilling the formulation 104. As shown, the formulation delivery system 100 includes a body portion 106 and a cap 108 coupled to the body portion 106. In the illustrated embodiment, the formulation delivery system 100 includes a seal 138 between the cap 108 and the body portion 106 suitable to seal formulation 104 within the interior portion, such as in the closed configuration illustrated in the FIG. 1B. In an embodiment, the cap 108 and body portion 106 are configured to cooperatively couple to place the cap 108 and the body portion 106 in a closed configuration, thereby retaining any formulation 104 within the interior portion of the formulation delivery system 100.

Figure 2A:
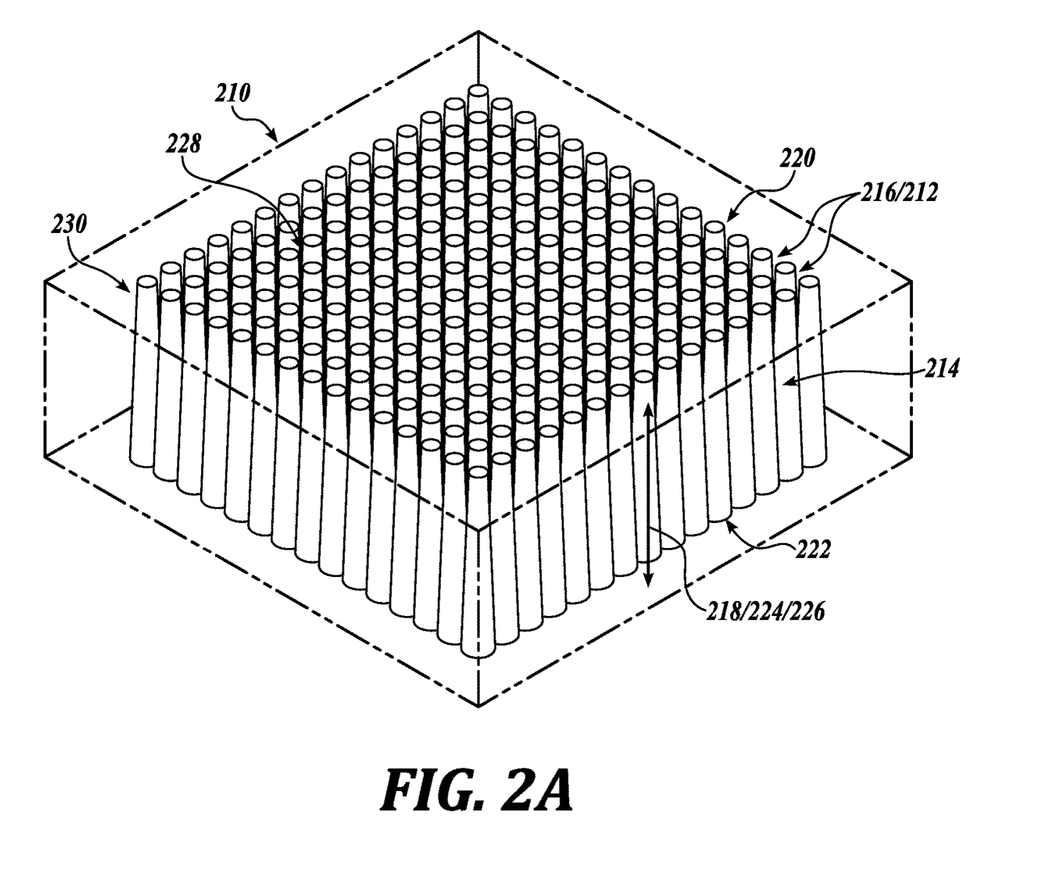
FIG. 2A is a perspective view of a porous formulation storage cushion, in accordance with an embodiment of the disclosure.
Figure 2B:
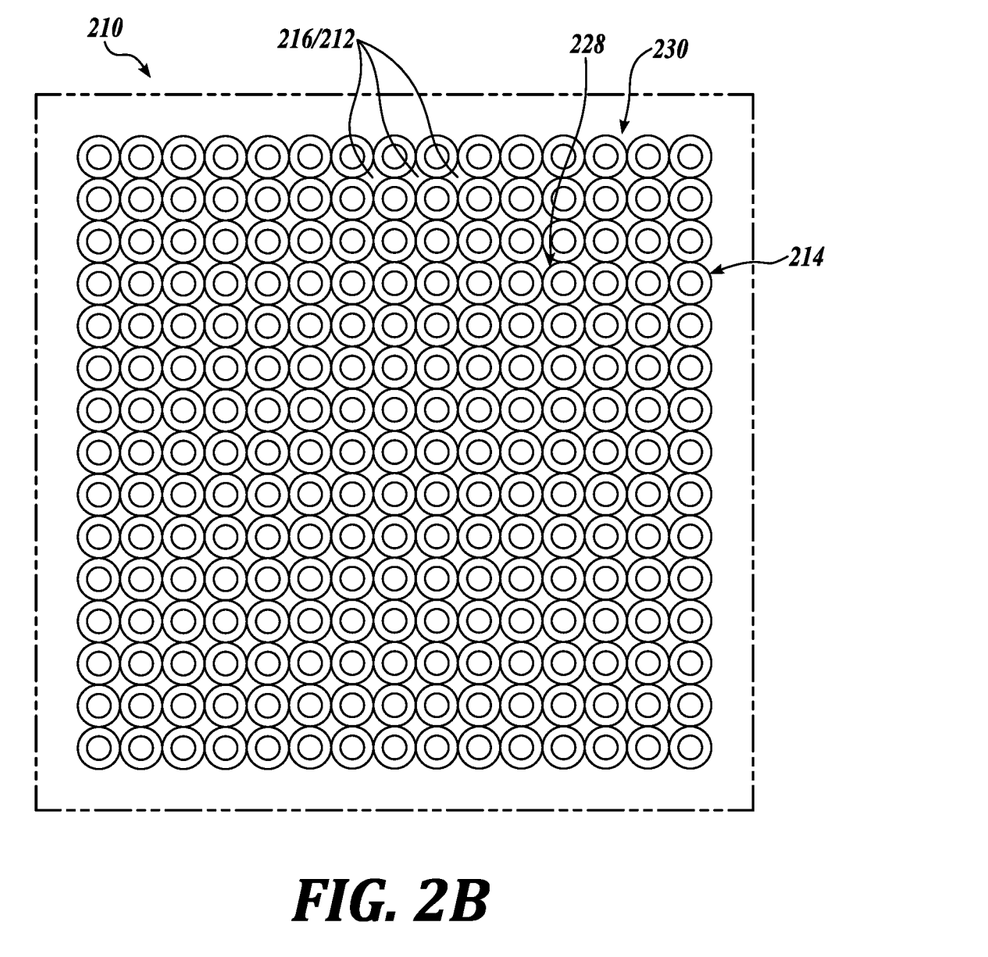
FIG. 2B is a top-down plan view of the porous formulation storage cushion of FIG. 2A.
Figure 2C:
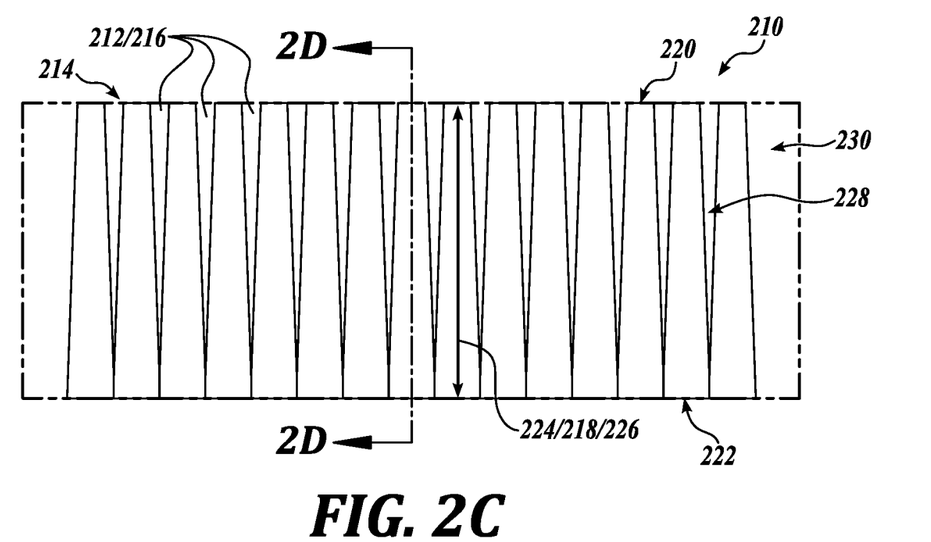
FIG. 2C is a side view of the porous formulation storage cushion of FIG. 2A.
Figure 2D:
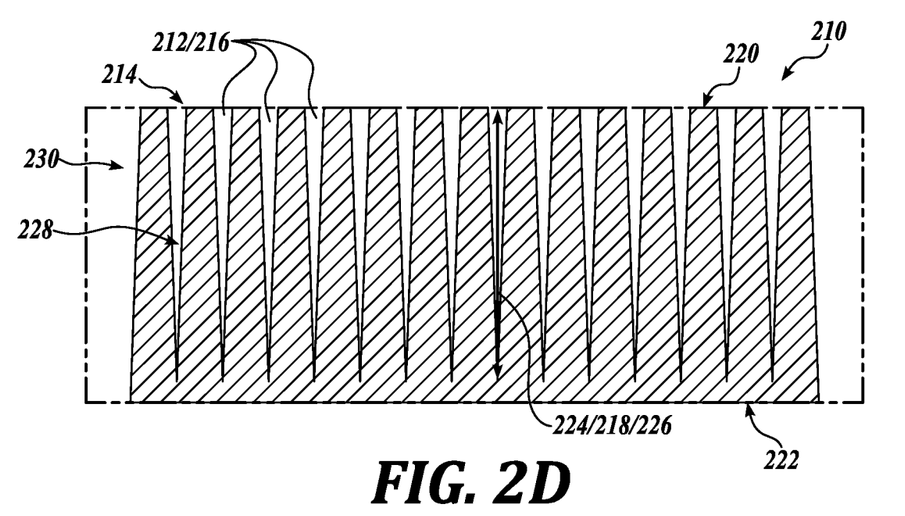
FIG. 2D is a cross-section view of the porous formulation storage cushion of FIG. 2A.

In an embodiment, the porous formulation storage cushion comprises a plurality of filaments. In that regard, attention is directed to FIGS. 2A-2D, in which a porous formulation storage cushion 210, in accordance with an embodiment of the disclosure, is illustrated. FIG. 2A is a perspective view of a porous formulation storage cushion 210, in accordance with an embodiment of the disclosure. FIG. 2B is a top-down plan view of the porous formulation storage cushion 210. FIG. 2C is a side view of the porous formulation storage cushion 210. FIG. 2D is a cross-sectional view of the porous formulation storage cushion 210. As shown, the filaments of the plurality of filaments 214 are coupled at one or more points to other neighboring filaments. Additionally, interstices 216 between individual filaments of the plurality of filaments 214 are shown to define the plurality of pores 212 of the porous formulation storage cushion 210. Such a porous storage formulation cushion 210 may be formed through additive manufacturing, such as by repeatedly depositing disk-like layers of material to define the plurality of filaments 214, as discussed further herein. In an embodiment, the illustrated porous formulation storage cushion 210 is an example of the porous formulation storage cushion 110 of FIGS. 1A and 1B.

In an embodiment, a thickness of filaments of the plurality of filaments 214 varies along a length 218 of the porous formulation storage cushion 210. In this regard, the plurality of filaments 214 tapers going from a base portion 222 of the porous storage formulation cushion 210 to an application surface 220. In this regard, the porous formulation storage cushion 210 is configured to define a pore-size gradient 224 and a pore-density gradient 226 and to provide a capillary force gradient. For example, the porous formulation storage cushion 210 is configured to wick a formulation with different capillary strength at the base portion 222 compared to at the application surface 220. While the pore-size gradient 224 and pore-density gradient is shown along varying along axes of the plurality of filaments, it will be understood that the porous formulation storage cushion 210 can be configured to define such gradients 224 and 226 along other axes, lengths, and the like of the porous formulation storage cushion 210, instead of or in addition to the illustrated gradients 224 and 226.

While the illustrated embodiment is shown to have filaments with a diameter smaller at the application surface 220 than at the base portion 222, it will be understood that other configurations are possible, such as where the filaments have a larger diameter at the application surface 220 than at the base portion 222. In this regard, the porous formulation storage cushion 210 may be configured to ensure that a consistent amount of formulation is loaded onto the application surface 220, due to strong capillary forces in the relatively narrow portions of the plurality of pores 212 adjacent to the application surface 220.

As shown, major axes of the plurality of filaments 214 are aligned. Correspondingly, the plurality of pores 212 are aligned along the major axes. In this regard, the porous formulation storage cushion 210 is configured to provide directional wicking of formulation. That is, the plurality of aligned filaments are configured to wick formulation along the common major axes of the plurality of filaments 214, such as from a base portion 222 of the porous formulation storage cushion 210 towards an application surface 220. In the illustrated embodiment, the direction of the major axes of the plurality of filaments 214 are orthogonal to the base portion 222. However, it will be understood that other configurations are possible, such as where major axes of the plurality of filaments 214 are non-orthogonal to the base portion 222.

The porous formulation storage cushion 210 is also shown to include an edge portion 230 that is free of pores. Accordingly, an application surface 220 of the porous storage formulation cushion defines a first portion 228 having a plurality of pores 212 configured to place the porous applicator in fluidic contact with the formulation and a second portion 230 free of pores. In this regard, the porous formulation storage cushion 210 is configured to provide formulation to certain portions of the porous applicator, such as those in contact with the first portion 228 of the porous formulation storage cushion 210, and not to others, such as those in contact with the second portion 230 of the porous formulation storage cushion 210. Likewise, in an embodiment, the porous formulation storage cushion 210 is configured to load a first portion of the porous applicator with a first amount of formulation and to load a second portion of the porous applicator with a second amount of formulation different than the first amount. Such selective delivery of formulation to the porous applicator may be suitable where patterned formulation application is desirable. While the portion 230 that is free of pores is shown to have a square perimeter around the porous portion 228, it will be understood that other shapes and configurations are possible, such as where the pore-free portion 230 defines another shape, such as a circle, a star, a triangle, a free shape, or the like. Likewise, while the porous formulation storage cushion 210 is shown to include a porous section 228 and a section free of pores 230, it will be understood that other configurations are possible, such as where the porous formulation storage cushion 210 defines a pore-density gradient disposed on the application surface 220.

Figure 3A:
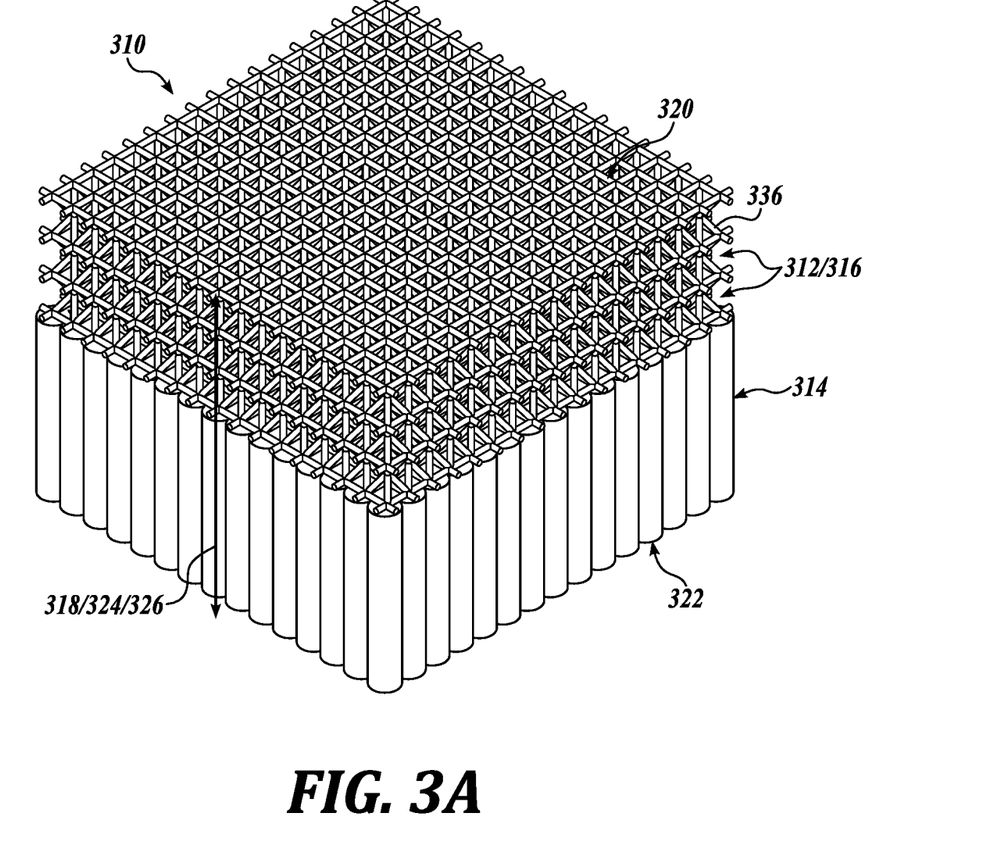
FIG. 3A is a perspective view of another porous formulation storage cushion, in accordance with an embodiment of the disclosure.
Figure 3B:
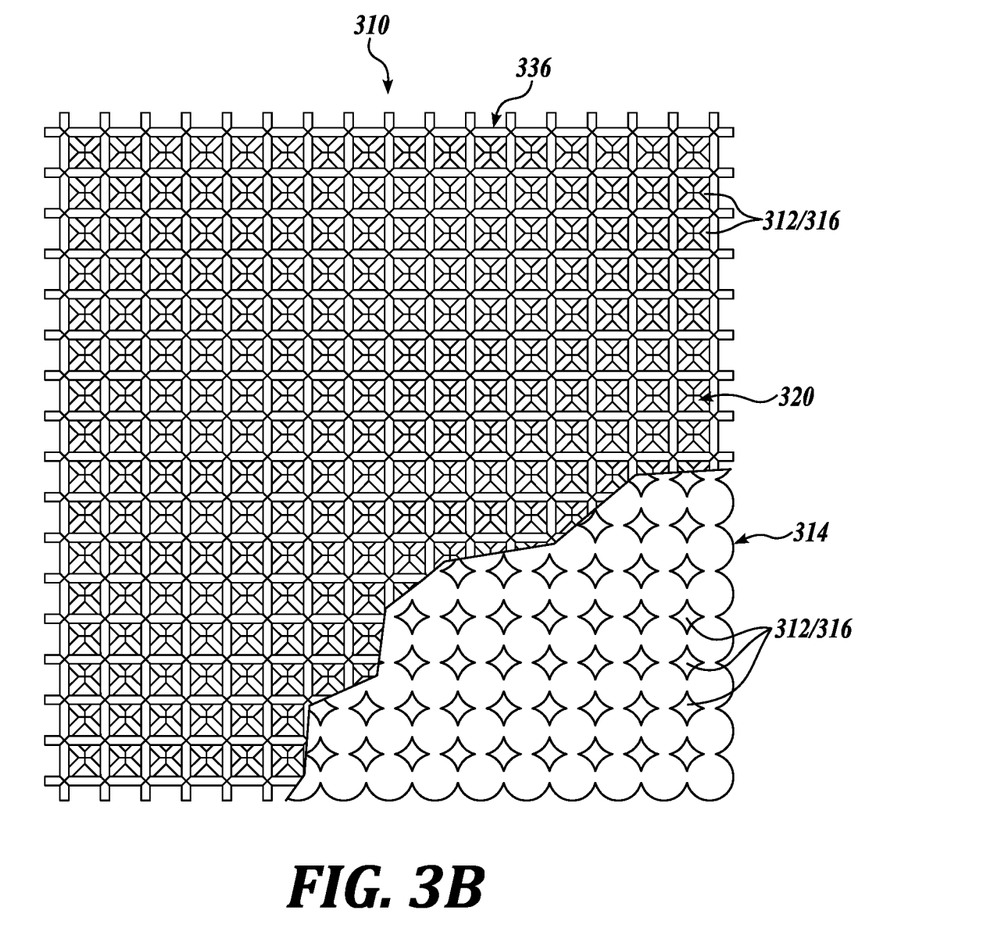
FIG. 3B is a top-down plan view of the porous formulation storage cushion of FIG. 3A with a partial cutaway.
Figure 3C:
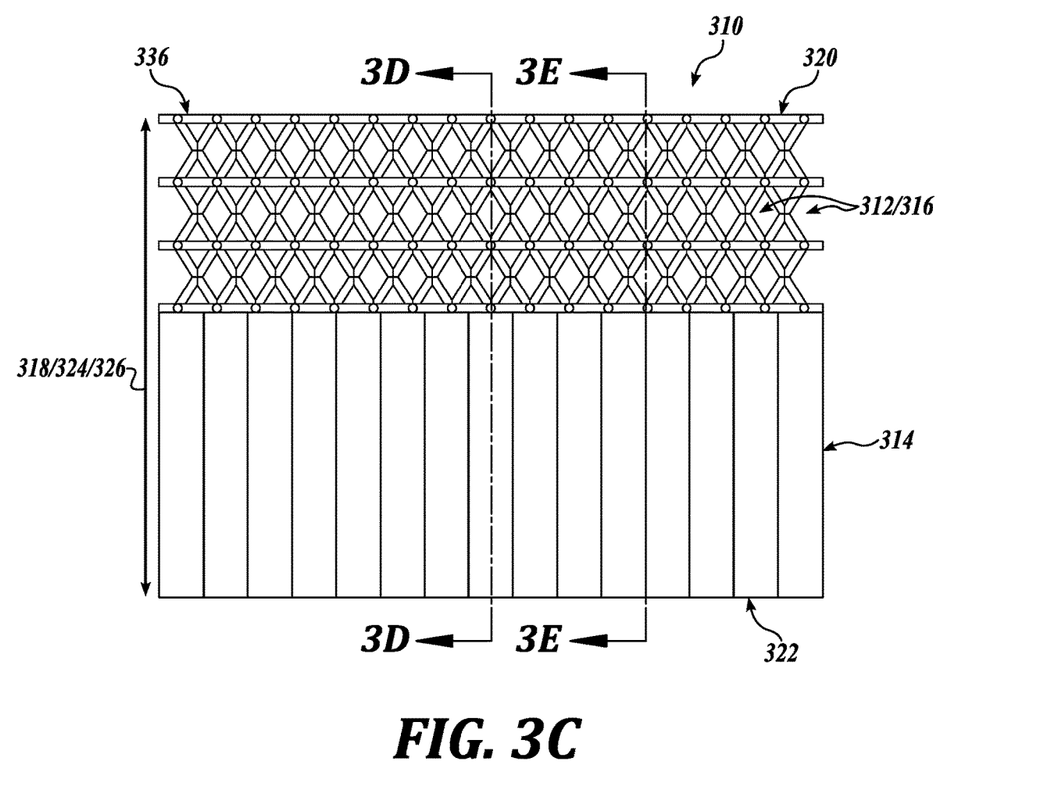
FIG. 3C is a side view of the porous formulation storage cushion of FIG. 3A.
Figure 3D:
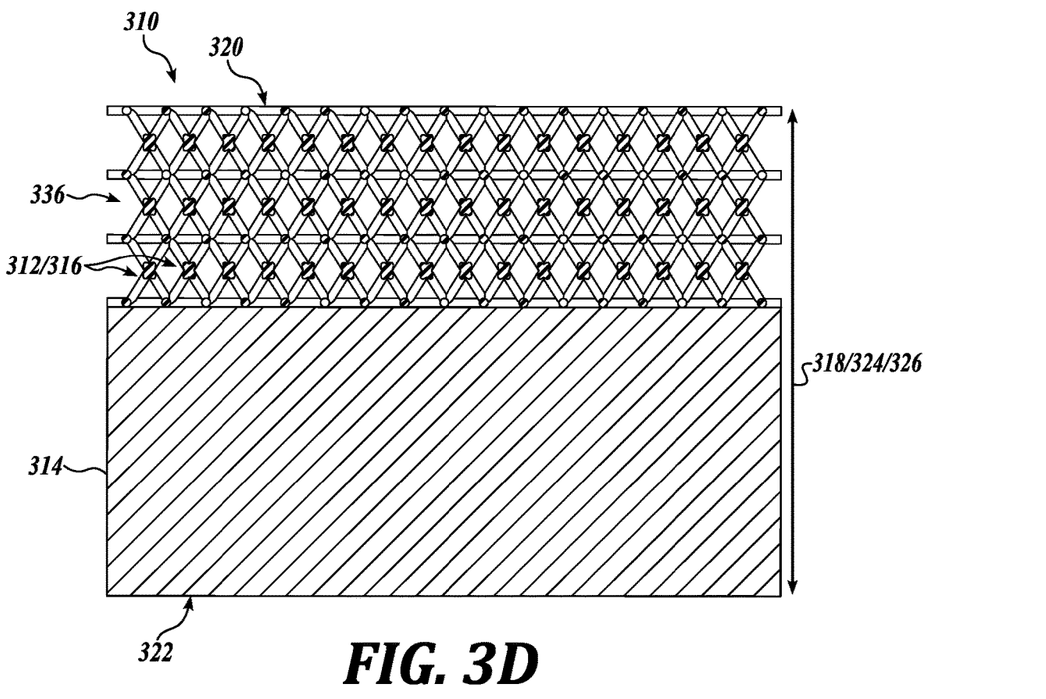
FIG. 3D is a cross-section view of the porous formulation storage cushion of FIG. 3A.
Figure 3E:
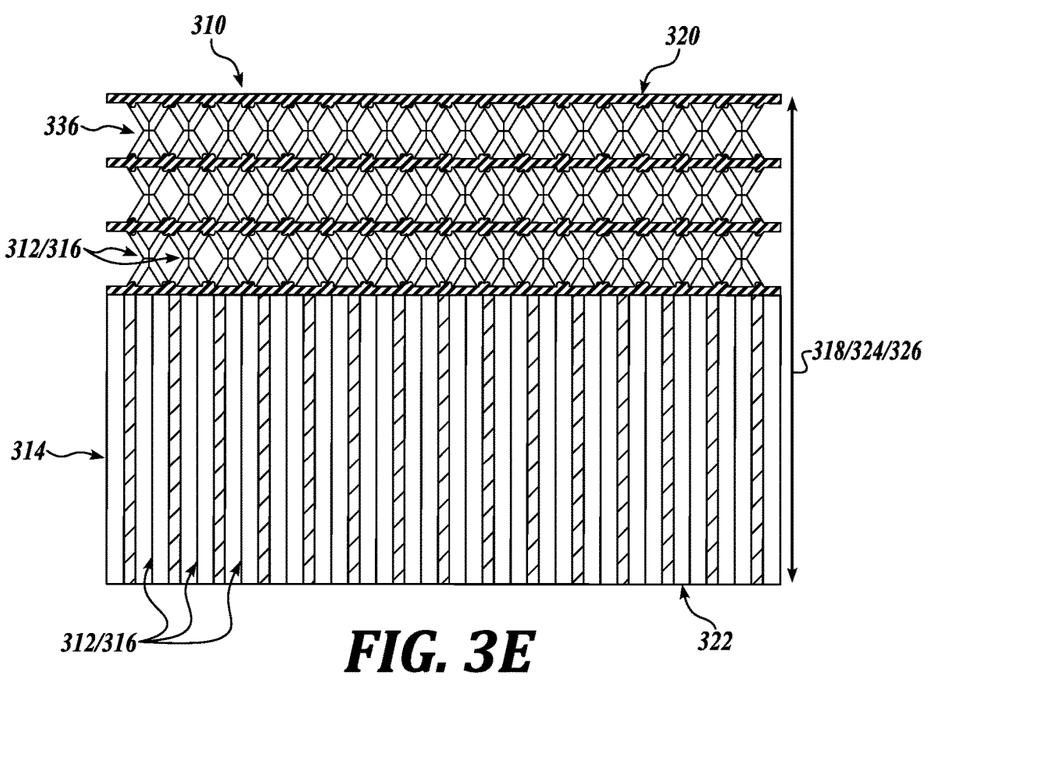
FIG. 3E is another cross section view of the porous formulation storage cushion of FIG. 3A.

In an embodiment, the porous formulation storage cushion comprises a plurality of filaments having substantially uniform diameter along a length of the porous formulation storage cushion. In that regard, attention is directed to FIGS. 3A-3E, in which a porous formulation storage cushion 310, in accordance with an embodiment of the disclosure is illustrated. FIG. 3A is a perspective view of a porous formulation storage cushion 310. FIG. 3B is a top-down plan view of the porous formulation storage cushion 310. FIG. 3C is a side view of the porous formulation storage cushion 310. FIG. 3D is a cross-section view of the porous formulation storage cushion 310. FIG. 3E is another cross section view of the porous formulation storage cushion 310. In an embodiment, the porous formulation storage cushion 310 is an example of the porous formulation storage cushion 110 of FIGS. 1A and 1B.

As shown, interstices 316 between individual filaments of the plurality of filaments 314 define the plurality of pores 312. Like the porous formulation storage cushion 210 of FIGS. 2A-2D, the porous formulation storage cushion 310 may be made through additive manufacturing, such as according to the methods described further herein. Further, as shown in, for example, FIG. 3E, a diameter of the filaments of the plurality of filaments 314 is substantially the same at a base portion 322 and at the application surface 320. In that regard, a size of the plurality of pores 312 defined by interstices 316 of the plurality of filaments 314 is consistent along a length 318 of the porous formulation storage cushion 310. Such evenly sized pores 312 may be suitable for even wicking of a formulation through the pores 312.

As shown in FIG. 3D, certain planes of the porous formulation storage cushion 310 do not provide access to the plurality of pores 312. In this regard, the porous formulation storage cushion 310 is configured to provide directional wicking of a formulation in that wicking generally does not occur or is substantially slowed along directions in which there are no pores.

The porous formulation storage cushion 310 is shown to further include a porous lattice 336. As shown, the porous lattice 336 is positioned to define a portion of the application surface 320. In this regard, the porous lattice 336 is configured to contact a porous applicator, such as to load the porous applicator with formulation as the porous lattice 336 is deformed. The porous lattice 336 may be made by additive manufacturing, such as according the methods described further herein. As shown, interstices 316 of the porous lattice 336 further defines pores 312, into which formulation may be disposed, such as through wicking of the formulation. In the illustrated embodiment, pores 312 defined by interstices 316 of the porous lattice 336 are larger than pores 312 defined by interstices 316 of the plurality of filaments 314. In this regard, the porous formulation storage cushion 310 is configured to define a capillary force gradient along length 318 due to the pore-size gradient 324 and or the pore-density gradient 326.

In an embodiment, the porous lattice 336 has a stiffness different from a stiffness of other portions of porous formulation storage cushion 310, such as the plurality of filaments 314. In that regard, the porous lattice 336 may have a first durometer and the plurality of filaments 314 may have a second durometer higher than the first durometer. Accordingly, the porous lattice 336 may be suitable to provide higher loading of the porous applicator with formulation than if the porous lattice 336 had a durometer the same as or lower than the plurality of filaments 314. The stiffness gradient may be due, at least in part, to difference in pore sizes, thickness of filaments, and the like in various portions of the porous formulation storage cushion 310.

In an embodiment, the porous formulation storage cushion defines a plurality of pores in which the pores are distributed randomly throughout the porous formulation storage cushion. In that regard, attention is directed to FIG. 4A, in which a porous formulation storage cushion 410A, in accordance with an embodiment of the disclosure, is illustrated. In an embodiment, the porous formulation storage cushion 410A is an example of the porous formulation storage cushion 110 of FIGS. 1A and 1B.

Figure 4A:
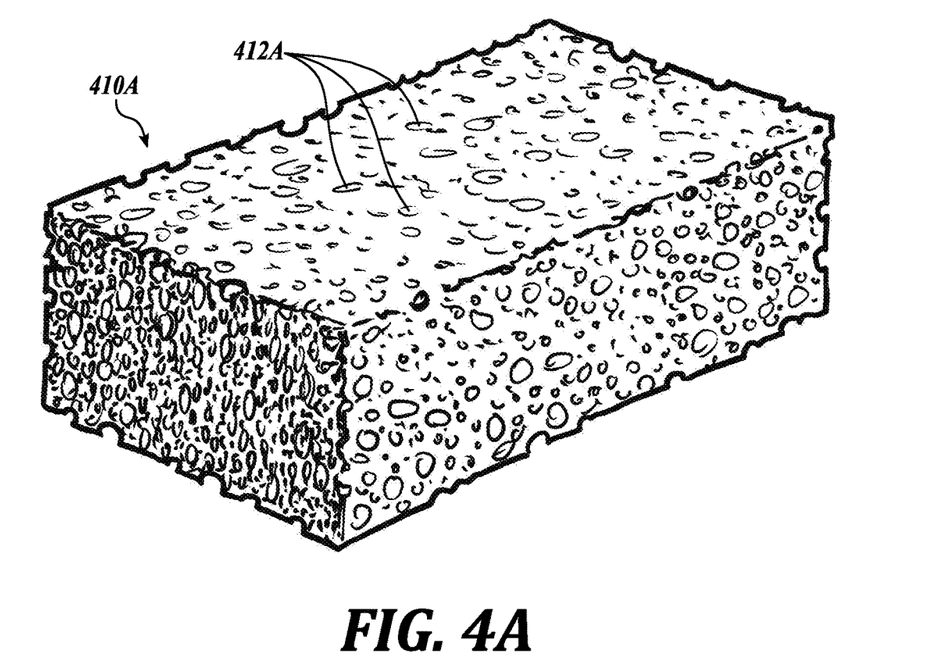
FIG. 4A is a perspective view of another porous formulation storage cushion, in accordance with an embodiment of the disclosure.

As shown, the porous formulation storage cushion 410A defines a plurality of pores 412A, shown here as a plurality of open cell pores 412A, randomly distributed throughout the porous formulation storage cushion 410A. In the illustrated embodiment, the pores 412A are randomly distributed both with respect to pore density and pore size. Such random distribution may be suitable for an even loading of formulation onto a porous applicator.

Figure 4B:
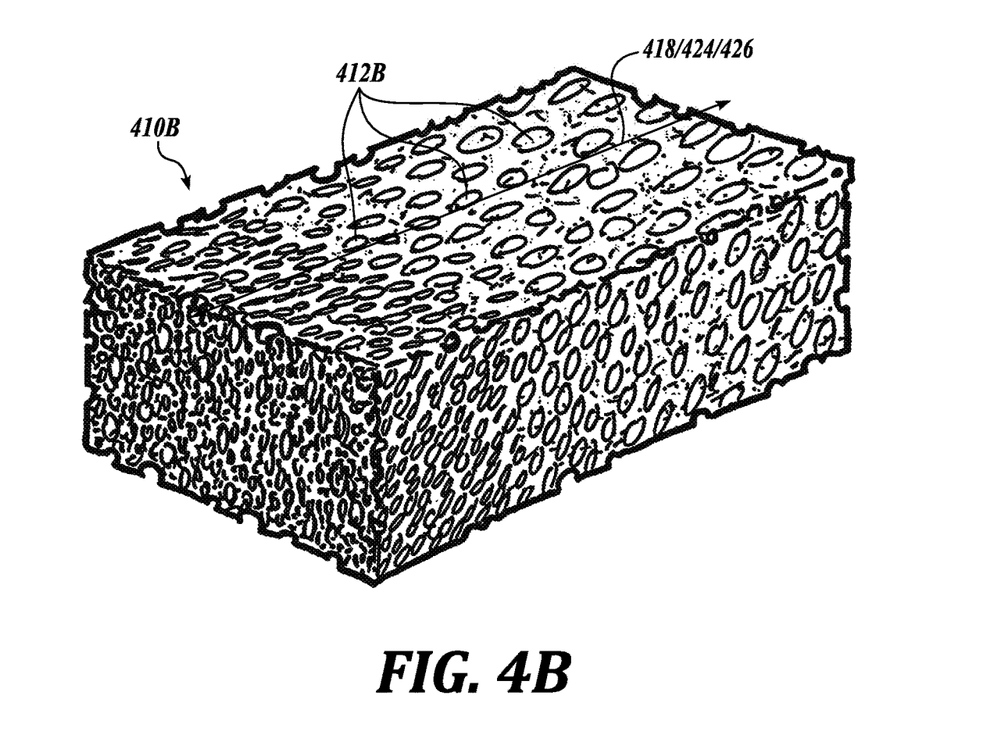
FIG. 4B is a perspective view of another porous formulation storage cushion, in accordance with an embodiment of the disclosure.

In an embodiment, a density or size of the plurality of pores defines a gradient across a length of the porous formulation storage cushion. In that regard, attention is directed to FIG. 4B, in which a porous formulation storage cushion 410B is illustrated. FIG. 4B is a perspective view of the porous formulation storage cushion 410B, in accordance with an embodiment of the disclosure. In an embodiment, the porous formulation storage cushion 410B is an example of the porous formulation storage cushion 110 of FIGS. 1A and 1B.

As shown, a size and a density of the plurality of pores 412B varies along length 418 to define a pore-size gradient 424 and a pore-density gradient 426, respectively. As discussed further herein, such gradients 424 and 426 may be suitable to provide a capillary force gradient for a formulation in contact with the porous formulation storage cushion 410B. In this regard, such gradients 424 and 426 may be suitable to load varying amounts of formulation into plurality of pores 412B. In this regard, the porous formulation storage cushion 410B is configured to load varying amounts of formulation into a porous applicator in contact with an application surface of the porous formulation storage cushion 410B along the gradients 424 and 426.

In another aspect, the present disclosure provides a method of making a porous formulation storage cushion. In an embodiment, the method includes additively manufacturing a porous formulation storage cushion, such as through the use of an additive manufacturing assembly.

In an embodiment, the method includes depositing a first layer of a material with an additive manufacturing assembly; and depositing a second layer of the material, such as on a surface of the first layer, with the additive manufacturing assembly. Such additive manufacturing can include, for example, vat photopolymerization, fused deposition modelling, sheet lamination, material jetting, binder jetting, powder bed fusion, directed energy deposition, and the like.

In an embodiment, the method includes depositing a plurality of layers of the material to define a plurality of pores. Such pores may be defined, at least in part, by depositing a plurality of filaments, the interstices of which define the plurality of pores. In an embodiment, the method includes depositing the material to define a plurality of filaments having major axes that are substantially parallel. As discussed further herein, such parallel or substantially parallel major axes may be suitable to provide directional wicking of a formulation through the porous formulation storage cushion. As discussed further herein with respect to FIGS. 5A-5D, layers may be additively and sequentially deposited parallel to major axes of the filaments or perpendicular to major axes of the filaments. As discussed further herein with respect to FIGS. 2A-2D, in an embodiment, a thickness of filaments of the plurality of filaments varies along a length of the porous formulation storage cushion. In one embodiment, as discussed further herein with respect to FIGS. 3A-3E, a thickness of the plurality of filaments is substantially even along a length of the porous formulation storage cushion. As discussed further herein, such variation of thickness, or lack thereof, can be used to tailor an amount of formulation loaded onto a porous applicator in contact with an application surface of the porous formulation storage cushion, such as due to the formation of capillary force gradient defined by pores of the porous formulation storage cushion.

In an embodiment, the method includes depositing, with the additive manufacturing assembly, a porous lattice, such as on an application surface of the porous formulation storage cushion. As above, such a porous lattice may have a stiffness lower than a stiffness of other portions of the porous formulations storage cushion, suitable to load a porous applicator with a greater amount of formulation.

In another aspect, the present disclosure provides a method of transporting a formulation. In an embodiment, the method is performed with a formulation delivery system and/or a porous formulation storage cushion as described herein. Such methods may be used to load a formulation into a porous applicator, such as for application to a portion of a body of a user.

In an embodiment, the method comprises transporting the formulation from a base portion of a porous formulation storage cushion through a plurality of pores to an application surface of the porous formulation storage cushion by capillary action; and transporting the formulation from the application surface through pores of a porous applicator. Such transportation into pores of the porous applicator may also be due to capillary action.

As discussed further herein with respect to the formulation delivery systems and porous formulation storage cushions of the present disclosure, the plurality of pores may be configured to define a capillary force gradient along a length of the porous formulation storage cushion. In that regard, the porous formulation storage cushion may define a first plurality of pores and a second plurality of pores, the second plurality of pores having a pore configuration, capillary force gradient, pore density, or fluid passage density different from the first plurality of pores.

In an embodiment, an application surface of the porous storage formulation cushion defines a first portion having a plurality of pores configured to place the porous applicator in fluidic contact with the formulation and a second portion free of pores. In this regard, the porous formulation storage cushion may be suitable for loading a first portion of the porous applicator in fluidic communication with the first portion of the porous formulation storage cushion with a first amount of formulation; and loading a second portion of the porous applicator in contact with the second portion of the porous formulation storage cushion with a second amount of formulation less than the first amount. Such loading of the porous applicator may be defined, at least in part, by the capillary force gradient.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

While illustrative embodiments have been illustrated and described, it will be appreciated that various changes can be made therein without departing from the spirit and scope of the claimed subject matter.

The embodiments of the invention in which a property or privilege is claimed are defined as follows:

1. A formulation delivery system, comprising:
   a porous applicator configured to absorb a formulation; and
   a porous formulation storage cushion defining a plurality of pores configured to absorb the formulation,
   wherein the plurality of pores is configured to define a capillary force gradient along a length of the porous formulation storage cushion,
   wherein the porous formulation storage cushion comprises a plurality of filaments,
   wherein filaments of the plurality of filaments define a major axis,
   wherein major axes of filaments of the plurality of filaments are aligned,
   wherein filaments of the plurality of filaments have a substantially uniform diameter along the length of the porous formulation storage cushion, and
   wherein filaments of the plurality of filaments are coupled at one or more points to adjacent filaments of the plurality of filaments.

2. The formulation delivery system of claim 1, wherein the porous formulation storage cushion comprises an additively manufactured porous structure.

3. The formulation delivery system of claim 1, wherein the porous formulation storage cushion defines a first plurality of pores and a second plurality of pores, the second plurality of pores having a pore configuration, capillary force gradient, pore density, or fluid passage density different from the first plurality of pores.

4. The formulation delivery system of claim 1, wherein the porous formulation storage cushion is carried by a body portion of the formulation delivery system.

5. The formulation delivery system of claim 1, wherein the porous formulation storage cushion comprises a porous sintered material.

6. The formulation delivery system of claim 1, wherein interstices between individual filaments of the plurality of filaments define the plurality of pores.

7. The formulation delivery system of claim 6, wherein the plurality of pores defined by the plurality of filaments is configured to provide a directional wicking of the formulation through the plurality of pores.

8. The formulation delivery system of claim 1, wherein the plurality of pores is configured to provide a fluidic communication between the porous applicator and the formulation when the porous applicator is in contact with an application surface of the porous formulation storage cushion.

9. The formulation delivery system of claim 1, wherein a size of individual pores of the plurality of pores defines a pore-size gradient along the length of the porous formulation storage cushion.

10. The formulation delivery system of claim 1, wherein a density of pores of the plurality of pores defines a pore-density gradient along the length of the porous formulation storage cushion.

11. The formulation delivery system of claim 1, wherein an application surface of the porous storage formulation cushion defines a first portion having the plurality of pores configured to place the porous applicator in fluidic contact with the formulation and a second portion free of pores.

12. The formulation delivery system of claim 1, further comprising the formulation carried by the body portion and in a fluidic communication with the plurality of pores.

13. The formulation delivery system of claim 12, wherein the plurality of pores is configured to wick the formulation through a capillary action.

14. The formulation delivery system of claim 1, wherein the porous formulation storage cushion is configured to load a first portion of the porous applicator with a first amount of formulation and to load a second portion of the porous applicator with a second amount of formulation different than the first amount.

15. The formulation delivery system of claim 1, wherein the porous formulation storage cushion varies in stiffness across the length of the porous formulation storage cushion.

16. The formulation delivery system of claim 1, wherein an application surface of the porous formulation storage cushion comprises a porous lattice configured to contact the porous applicator.

17. The formulation delivery system of claim 16, wherein the porous lattice has a stiffness different than a stiffness of other portions of the porous formulation delivery storage cushion.

18. A method of additively manufacturing a porous formulation storage cushion defining a plurality of pores configured to absorb a formulation, the method comprising:
   depositing a first layer of a material with an additive manufacturing assembly; and
   depositing a second layer of the material with the additive manufacturing assembly to define a plurality of pores,
   wherein the plurality of pores is configured to define a capillary force gradient along a length of the porous formulation storage cushion,
   wherein the porous formulation storage cushion comprises a plurality of filaments,
   wherein filaments of the plurality of filaments define a major axis,
   wherein major axes of filaments of the plurality of filaments are aligned,
   wherein filaments of the plurality of filaments have a substantially uniform diameter along the length of the porous formulation storage cushion, and
   wherein filaments of the plurality of filaments are coupled at one or more points to adjacent filaments of the plurality of filaments.

19. The method of claim 18, wherein interstices between individual filaments of the plurality of filaments define the plurality of pores.

20. The method of claim 18, wherein a size of individual pores of the plurality of pores defines a pore-size gradient along the length of the porous formulation storage cushion.

21. The method of claim 18, further comprising depositing, with the additive manufacturing assembly, a porous lattice to define an application surface of the porous formulation storage cushion.

22. A method of transporting a formulation, the method comprising:
 transporting the formulation from a base portion of a porous formulation storage cushion through a first plurality of pores to an application surface of the porous formulation storage cushion by capillary action; and
 transporting the formulation from the application surface through pores of a porous applicator,
 wherein the first plurality of pores is configured to define a capillary force gradient along a length of the porous formulation storage cushion,
 wherein the porous formulation storage cushion comprises a plurality of filaments,
 wherein filaments of the plurality of filaments define a major axis,
 wherein major axes of filaments of the plurality of filaments are aligned,
 wherein filaments of the plurality of filaments have a substantially uniform diameter along the length of the porous formulation storage cushion, and
 wherein filaments of the plurality of filaments are coupled at one or more points to adjacent filaments of the plurality of filaments.

23. The method of claim 22, wherein the porous formulation storage cushion defines the first plurality of pores and a second plurality of pores, the second plurality of pores having a pore configuration, capillary force gradient, pore density, or fluid passage density different from the first plurality of pores.

24. The method of claim 22, wherein the application surface of the porous storage formulation cushion defines a first portion having the first plurality of pores configured to place the porous applicator in fluidic contact with the formulation and a second portion free of pores.

25. The method of claim 24, further comprising:
 loading a first portion of the porous applicator in fluidic communication with the first portion of the porous formulation storage cushion with a first amount of formulation; and
 loading a second portion of the porous applicator in contact with the second portion of the porous formulation storage cushion with a second amount of formulation less than the first amount.

26. The method of claim 25, wherein loading of the porous applicator is defined, at least in part, by the capillary force gradient.

27. The method of claim 22, wherein interstices between individual filaments of the plurality of filaments define the first plurality of pores.

28. The formulation delivery system of claim 1, wherein a plurality of lines of declination are disposed perpendicular to a major axis of filaments of the plurality of filaments.

29. The formulation delivery system of claim 1, wherein a plurality of lines of declination are disposed parallel to a major axis of filaments of the plurality of filaments.

\* \* \* \* \*